United States Patent [19]

Sasaki

[11] 4,242,089

[45] Dec. 30, 1980

[54] DENTAL PROSTHESIS

[76] Inventor: Hideki Sasaki, 53, 3-chome, Kuramotomoto-machi, Tokushima-shi, Tokushima-ken, Japan

[21] Appl. No.: 75,540

[22] Filed: Sep. 13, 1979

Related U.S. Application Data

[63] Continuation of Ser. No. 839,477, Oct. 4, 1977, abandoned.

[51] Int. Cl.³ .............................................. A61C 13/22
[52] U.S. Cl. ................................................... 433/189
[58] Field of Search ......................................... 433/189

[56] References Cited

U.S. PATENT DOCUMENTS

| 3,798,770 | 3/1976 | Mitchell | 433/189 |
| 4,056,411 | 11/1977 | Chew | 148/31.57 |

FOREIGN PATENT DOCUMENTS

| 2029344 | 1/1969 | France | 433/189 |
| 2076270 | 7/1970 | France | 433/189 |
| 2308348 | 12/1976 | France | 433/189 |

*Primary Examiner*—Robert Peshock
*Attorney, Agent, or Firm*—Fred Philpitt

[57] ABSTRACT

This invention relates to the use of palladium-cobalt alloys as a magnetizable material in connection with dental prosthesis.

2 Claims, 3 Drawing Figures

DENTAL PROSTHESIS

This is a continuation of application Ser. No. 839,477, filed Oct. 4, 1977 and now abandoned.

BACKGROUND

There are quite a few patents which broadly pertain to the concept of maintaining artificial teeth or dentures in place by means of magnetic means. Coacting magnetic materials are mounted in both the artificial tooth (or denture) and in the gum or jawbone so that magnetic forces will draw the artificial tooth (or denture) to the tooth root set in the gum or jawbone. A few examples of such U.S. Pat. Nos. are 2,709,301; 3,646,676 and 3,798,770.

THE PRESENT INVENTION

I have discovered that palladium-cobalt alloys are highly useful as a magnetizable material in connection with the magnetic type of dental prothesis. My discovery has the advantage of lower cost and long life. Dentures made in accordance with my invention can be easily cleaned and do not adversely affect other teeth.

Figure 1:
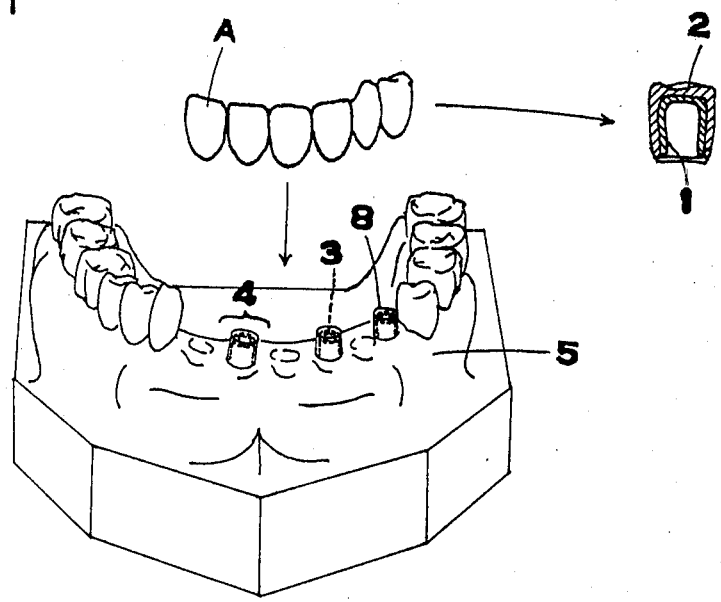
FIG. 1 is a perspective view of a tooth, gum and crown arrangement in accordance with this invention.

In accordance with one embodiment of my invention a magnetic material can be imbedded in the tooth root set in the gum or alveolar bone and the artificial tooth or denture is then provided with a palladium-cobalt alloy. This embodiment is illustrated in FIG. 1 wherein A is a denture or crown consisting of artificial teeth composed of a palladium-cobalt alloy 1 that has been fused on the inside or porcelain 2. The melting point of palladium-cobalt alloy is about 1230° C. and the fusing can easily be done by a dentist. Palladium-cobalt alloys have better corrosion properties than gold-palladium alloys and are less expensive. A magnet 3 and an inner crown 8 of non-magnetic material serve as an abutment member over which the artificial tooth fits. Magnetic forces hold them together.

Figure 2:
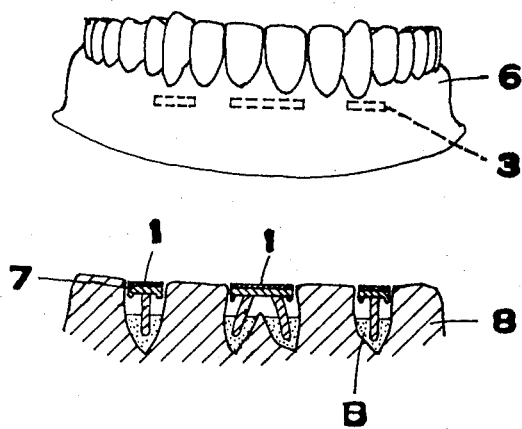
FIG. 2 shows a front view of a denture plate and magnet arrangement, and a sectional view showing how a Pd-Co alloy on a root cap is fixed in a tooth root.

In accordance with a second embodiment of my invention a magnet is imbedded in the denture or artificial tooth and a palladium-cobalt alloy is imbedded in the alveolar bone. This embodiment is illustrated in FIG. 2 wherein 3 is a magnet imbedded in a denture plate 6 and a palladium-cobalt alloy 1 attached to a root cap 7 is imbedded in the tooth root B of the alveolar bone 8. When the denture plate 6 is brought close to the root cap 7 magnetic forces hold them together.

Figure 3:
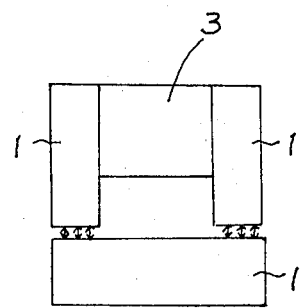
FIG. 3 shows the cooperative relationship between a magnet and a Pd-Co alloy.

FIG. 3 illustrates that by surrounding a magnet 3 with palladium-cobalt alloy the magnetic forces do not affect the body and no bad effects of the magnet can occur.

I claim:

1. An artificial tooth arrangement comprising in combination:
   (a) a denture plate (6) having a magnet (3) embedded therein,
   (b) a root cap (7) which is adapted to be imbedded in a tooth root (B), and
   (c) a palladium-cobalt alloy attached to the upper surface of the root cap (7).

2. An artificial tooth arrangement comprising in combination:
   (a) a denture or crown (A) composed of concave palladium-cobalt alloys (1) that have been fused on the inside of porcelain (2),
   (b) projecting inner crowns (8) of non-magnetic material serve as abutment members imbedded in the tooth root set, and
   (c) magnets (3) fixed in each of the said inner crowns (8).

* * * * *